United States Patent [19]

Throckmorton

[11] 4,331,817

[45] May 25, 1982

[54] PROCESS FOR THE PREPARATION OF 4-ARYLTHIOANILINES

[75] Inventor: James R. Throckmorton, Woodbury, Minn.

[73] Assignee: Minnesota Mining and Manufacturing Co., Saint Paul, Minn.

[21] Appl. No.: 225,739

[22] Filed: Jan. 16, 1981

[51] Int. Cl.³ .................... C07C 85/00; C07C 85/24
[52] U.S. Cl. .................................. 564/430; 564/437
[58] Field of Search ......................................... 564/430

[56] References Cited

U.S. PATENT DOCUMENTS 3,948,987  4/1976  Fridinger ....................... 260/556 F

FOREIGN PATENT DOCUMENTS 2041369  9/1980  United Kingdom ................ 564/430

OTHER PUBLICATIONS

Fridinger, "Chem. Ab.," vol. 91, Ab. No. 84828r (1979).

Primary Examiner—John Doll
Attorney, Agent, or Firm—Cruzan Alexander; Donald M. Sell; Donald C. Gipple

[57] ABSTRACT

A process for the preparation of a 4-arylthioaniline from the corresponding 4-unsubstituted aniline which comprises reacting the latter with an alkali metal thiocyanate in the presence of halogen to provide the 4-thiocyanoaniline, reacting it with an alkali metal sulfide to convert the thiocyano moiety to an alkali metal mercaptide group followed by heating with cuprous oxide then with an aryl halide to form the desired product.

6 Claims, No Drawings

PROCESS FOR THE PREPARATION OF 4-ARYLTHIOANILINES

BACKGROUND OF THE INVENTION

This invention relates to a process for the preparation of 4-arylthioanilines of the formula

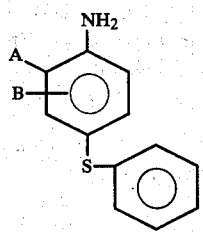

wherein A is halogen or CF₃ and B is hydrogen or halogen from 4-unsubstituted anilines of the formula

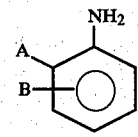

The products I can be converted directly to the corresponding 4-phenylthioalkanesulfonanilides of the formula

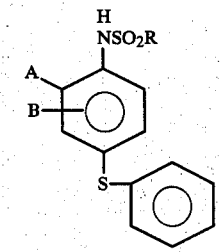

wherein A and B are as previously defined and R can be an alkyl group containing from 1 to 4 carbon atoms or monohalomethyl. These compounds (III) are known herbicidal and plant growth modifying agents. Thus, see U.S. Pat. No. 3,948,987 and British patent application No. 8002852 (filed Jan. 28, 1980, published Sept. 10, 1980 under Ser. No. 2,041,369A and corresponding to U.S. application Ser. No. 7,026 filed Jan. 29, 1979).

The present invention relates to a process for the preparation of 4-arylthioanilines of the formula

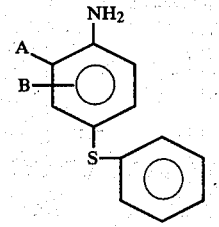

wherein A is halogen or trifluoromethyl and B is hydrogen or halogen which comprises (1) reacting a substituted aniline of the formula

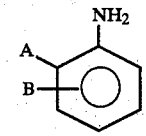

with an alkali metal thiocyanate in the presence of halogen to provide the corresponding 4-thiocyanoaniline:

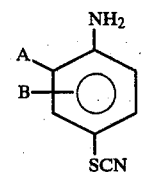

(2) mixing a solution of that compound in a solvent with a concentrated aqueous alkali metal sulfide solution to form the corresponding alkali metal mercaptide

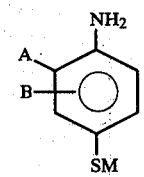

wherein M is an alkali metal atom;

(3) heating the reaction mixture containing the alkali metal mercaptide with cuprous oxide to form the cuprous mercaptide salt

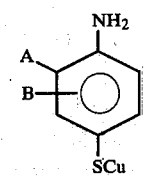

in situ; and (4) treating the heated reaction mixture with an aryl halide to form the desired product.

A particularly valuable aspect of the invention relates to the process of steps (2), (3) and (4), supra, for reasons given hereinafter.

This process offers advantages in the availability and cost of precursors over the known processes for the preparation of compounds III (shown in the patents just cited) and in overall high yield. In addition, the process is easily carried out at moderate temperatures, at atmospheric pressure (if desired) and without special production equipment.

The process can be characterized schematically as follows

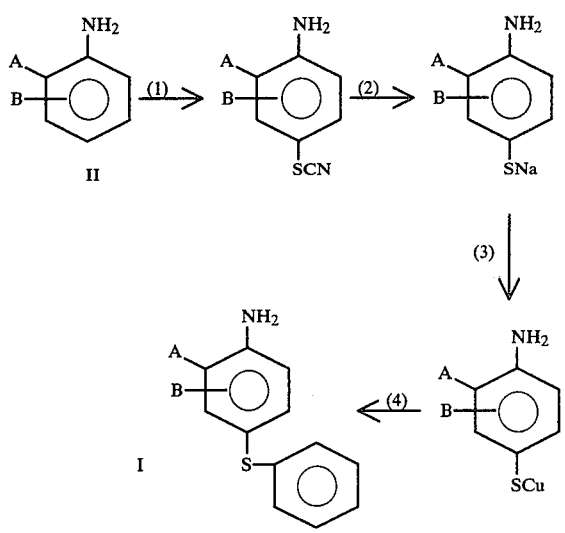

Normal molar proportions of the reactants can be utilized, although excesses of particular materials are often utilized to maximize yields. A less than molar proportion of cuprous oxide can be utilized when steps (3) and (4) are being carried out together in the reaction mixture since cuprous ion is released when the reaction of step (4) takes place thus releasing it for reuse in step (3). The amount of solvent is generally adjusted to achieve total solubility of the reactants under the conditions being utilized.

The starting materials for step (1) are, in general, commercially available. The thiocyanation is para-directing with respect to the amine group in the precursor and halo and $CF_3$ substituents on the other ring positions do not interfere with the reaction, which normally occurs in high yields, sometimes approaching theoretical. Conveniently, a solution of the precursor analine and an excess of sodium or potassium thiocyanate in methanol is mixed with bromine or chlorine. The temperature is maintained in the range of about 0°–45° C. in order to maintain solution of the reactants. When chlorine is utilized in this step, the gas is ordinarily passed directly into the solution while bromine is added dropwise. Alternatively, a solution of bromine in methanol saturated with sodium bromide can be added dropwise to the aniline-thiocyanate solution. When the reaction is substantially complete, the mixture is neutralized and the solid substituted 4-thiocyanoaniline product is collected, purified and dried.

Steps (2), (3) and (4) are preferably carried out in the same reaction vessel without removing or separating the constituents until the final product (I) has been prepared (although this is not necessary). Step (2) involves the formation of the alkali metal (sodium or potassium) mercaptide from the thiocyanoaniline, preferably by adding a solution of the latter in dimethylformamide to a concentrated solution of the alkali metal sulfide in water. The reaction is advantageously run in an inert atmosphere and is warmed for a time, e.g., at about 50° C.

Steps (3) and (4) are ordinarily carried out together by heating the aqueous dimethylformamide solution, normally at the reflux temperature of the mixture (in the range of about 150°–170° C. in most cases) for several hours with cuprous oxide and an excess of an aryl halide, preferably iodobenzene or bromobenzene to maximize the yield.

The dimethylformamide (which is the normally preferred solvent) can if desired be replaced by dimethyl sulfoxide or by a mixture of quinoline and pyridine. The solvent is chosen to boil in the range of about 150°–170° C.

Although the reagents for steps (3) and (4) may be added at the same time, the reactions themselves take place in order, and if the cuprous oxide is omitted the desired 4-phenylthioaniline is not formed. However, when carried out as described herein, the overall yields of steps (2), (3) and (4) is ordinarily very high, often approaching quantitative.

The following examples are provided to illustrate the practice of the process of the invention. Example 1 illustrates step (1) of the process and example 2 illustrates steps (2), (3) and (4). Example 3 shows that cuprous oxide is essential to the practice of the process.

EXAMPLE 1

2-Bromo-4-thiocyanoaniline

To a cold (0°–5° C.), stirred solution of o-bromoaniline (20.6 g., 0.12 mole) and sodium thiocyanate (29.2 g., 0.36 mole) in methanol (300 ml.) is added dropwise a solution of bromine (19.5 g., 0.122 mole) in methanol (75 ml.) saturated with sodium bromide. The solution is stirred for one hour following the addition of the bromine and then poured into water (2 liters) and neutralized with sodium carbonate. The resulting solid is collected, washed with water and dried, m.p. 74°–79° C., yield 96% of theoretical.

The following compounds are prepared using the same general method:
2-chloro-4-thiocyanoaniline, m.p. 63°–65° C.
2-fluoro-4-thiocyanoaniline, m.p. 34°–35° C.
2,5-dichloro-4-thiocyanoaniline, m.p. 111°–115° C.
2,3-dichloro-4-thiocyanoaniline, m.p. 132°–137° C.

EXAMPLE 2

2-Bromo-4-phenylthioaniline

A solution of 2-bromo-4-thiocyanoaniline (91.6 g., 0.4 mole) and dimethylformamide is added dropwise to a solution of sodium sulfide (0.48 mole) and water, under nitrogen, and the resulting solution is heated at 50° C. for one hour. Cuprous oxide (34.33 g., 0.24 mole) and iodobenzene (97.9 g., 0.48 mole) are added and the mixture is heated at a heating bath temperature of 150° C. for 4.5 hours. The reaction is quenched with water, methylene chloride is added and the resulting mixture is filtered through filter aid to remove suspended solids. The aqueous and organic layers are separated, and the aqueous layer is extracted three times with methylene chloride. The methylene chloride extracts are combined, washed with water and dried. Removal of the drying agent and methylene chloride gives the desired product in 95% of the theoretical yield. A purified sample melts at 61°–63° C.

| Analysis: | % C | % H | % N |
|---|---|---|---|
| Calculated for $C_{12}H_{10}BrNS$: | 51.44; | 3.6; | 5.0 |
| Found: | 51.9; | 3.6; | 5.0. |

The following compounds can be prepared utilizing the same general procedure:
2-chloro-4-phenylthioaniline, a solid.

2-fluoro-4-phenylthioaniline, a solid.
2,3-dichloro-4-phenylthioaniline, a solid.
2,5-dichloro-4-phenylthioaniline, a solid.

EXAMPLE 3

The process of Example 2 is repeated exactly except that the cuprous oxide is omitted. Although the heating of the final reaction mixture is continued for 24 hours at 150° C., no 2-bromo-4-phenylthioaniline product is formed.

What is claimed is:

1. A process for the preparation of 4-arylthioanilines of the formula

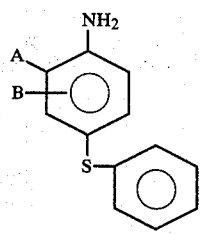

wherein A is halogen or trifluoromethyl and B is hydrogen or halogen which comprises (1) reacting a substituted aniline of the formula

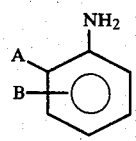

with an alkali metal thiocyanate in the presence of halogen to provide the corresponding 4-thiocyanoaniline:

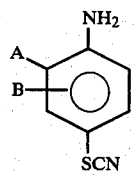

(2) mixing a solution of that compound in a solvent with a concentrated aqueous alkali metal sulfide solution to form the corresponding alkali metal mercaptide

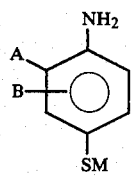

wherein M is an alkali metal atom;

(3) heating the reaction mixture containing the alkali metal mercaptide with cuprous oxide to form the cuprous mercaptide salt

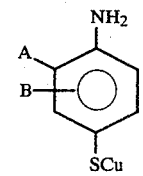

in situ; and (4) treating the heated reaction mixture with an aryl halide to form the desired product.

2. A process according to claim 1 in which the alkali metal thiocyanate is sodium thiocyanate and the alkali metal sulfide is sodium sulfide.

3. A process according to claim 2 in which A is bromine and B is hydrogen.

4. A process for the preparation of 4-arylthioanilines of the formula

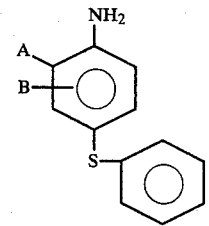

wherein A is halogen or trifluoromethyl and B is hydrogen or halogen which comprises (1) mixing a solution of a 4-thiocyanoaniline of the formula:

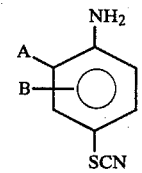

in a solvent with a concentrated aqueous alkali metal sulfide solution to form the corresponding alkali metal mercaptide

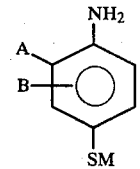

wherein M is an alkali metal atom;

(2) heating the reaction mixture containing the alkali metal mercaptide with cuprous oxide to form the cuprous mercaptide salt

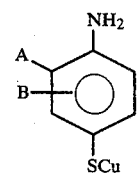

in situ; and (3) treating the heated reaction mixture with an aryl halide to form the desired product.

5. A process according to claim 4 in which the alkali metal sulfide is sodium sulfide.

6. A process according to claim 5 in which A is bromine and B is hydrogen.

* * * * *